US005402775A

United States Patent [19]

Reneau

[11] Patent Number: 5,402,775

[45] Date of Patent: Apr. 4, 1995

[54] MOUNTING STRUCTURE FOR A CYLINDRICAL WINDOW SECTION OF A PRESSURE VESSEL

[76] Inventor: Raymond P. Reneau, 701 N. St. Mary's St. #27, San Antonio, Tex. 78205

[21] Appl. No.: 118,003

[22] Filed: Sep. 8, 1993

[51] Int. Cl.[6] ...................... A61M 16/02; A61G 10/02

[52] U.S. Cl. .................................. 128/202.12; 600/21

[58] Field of Search ...................... 128/202.12, 200.24; 220/4.21, 4.24; 49/40, 41; 600/21

[56] References Cited

U.S. PATENT DOCUMENTS 4,467,798 8/1984 Saxon et al. .................... 128/205.26

FOREIGN PATENT DOCUMENTS 1506931 11/1967 France .................................. 600/21

1681854 10/1991 U.S.S.R. ......................... 128/202.12

1710041 2/1992 U.S.S.R. ......................... 128/202.12

OTHER PUBLICATIONS

Perry Baromedial Services brochure entitled "Sigma I—Monoplace Hyperbaric System", (unknown date).

Sechrist Industries, Inc. brochure entitled "Sechrist Monoplace Hyperbaric Systems", P/N 100028, rev. O (unknown date).

Reneau, Inc. brochure entitled "The Renau Unit", 1983.

*Primary Examiner*—Edgar S. Burr

*Assistant Examiner*—Eric P. Raciti

*Attorney, Agent, or Firm*—Glaser, Griggs & Schwartz

[57] ABSTRACT

A mounting structure for a cylindrical window section of a pressure vessel, wherein the mounting structure includes a cylindrical outer band, a mounting block mountable within the cylindrical outer band, securing members for securing the outer band and mounting block a predetermined fixed axial distance from the end portion of the pressure vessel, and a seal member for axial movement with respect to the outer band for maintaining sealable engagement of the cylindrical window section between the seal member and the end portion of the pressure vessel.

38 Claims, 4 Drawing Sheets

MOUNTING STRUCTURE FOR A CYLINDRICAL WINDOW SECTION OF A PRESSURE VESSEL

FIELD OF THE INVENTION

The field of this invention relates to mounting structures utilized in properly positioning and sealably mounting a cylindrical window section of a pressure vessel.

BACKGROUND OF THE INVENTION

Pressure vessels capable of withstanding elevated pressures have long been constructed of high strength, readily available materials such as stainless steel and the like. However, with the advent of expanded uses for pressure vessels, for example as in hyperbaric medicine, the desirability of having pressure vessels made of materials other than steel has increased. As in the case of hyperbaric medicine, and more particularly with hyperbaric chambers, it is desirable to have a hyperbaric chamber constructed in such a fashion that the patient attendant has good visual monitoring of the activities of the patient undergoing hyperbaric treatment. As such, it is desirable to have windows or view ports to accommodate such constant monitoring of the patient's progress during hyperbaric treatments.

Some prior art hyperbaric pressure vessels have utilized a basic stainless steel, tubular body section having a plurality of view ports to permit attendant visual contact with a patient within such a chamber, such as those units manufactured by Reneau, Inc. of Stafford, Texas and known as "The Reneau Unit".

On the other hand, other manufacturers of hyperbaric pressure vessels have chosen to manufacture hyperbaric pressure vessels utilizing cylindrical window sections that extend along the entire length of the pressure vessel, with such window sections being tightly secured between the end portions of the pressure vessel. Pressure vessels of this type are manufactured by Sechrist Industries, Inc. of Anaheim, California.

With the advent of the use of polymeric materials that are adapted to be formed into cylindrical window sections useful in hyperbaric chambers, it is desirable that such window sections be capable of being maintained in a sealable relation with the various components of the pressure vessel when at elevated pressures, while also being able to accommodate not only variations due to pressure differential but also variations to thermal gradients. Furthermore, with pressure vessels of the type that are formed of an entirely cylindrical window section, such as the Sechrist unit mentioned above, all connectible chamber utilities must of necessity be plumbed through the end portions of the chamber, as the structural integrity (and the related various pressure vessel code requirements) of the polymeric cylindrical window sections is not such that connections and utilities are capable of being plumbed through the cylindrical window section itself. Also, in view of the inability to form any types of openings through the walls of the cylindrical window section, there are no internal chamber mounting surfaces for mounting chamber utilities, such as patient handrails, supports for fluids (i.e., I.V.'s), mounting of electrical leads for electronic monitoring equipment and like medical apparatus. Furthermore, support for prior art cylindrical window section pressure vessels must come principally through the end portions of the pressure vessel rather than directly engaging the exterior surface of cylindrical window section itself; such engagement may cause localized stress concentrations and/or localized deformation, either of which may compromise the integrity of the pressure vessel.

Thus, so far as known, no pressure vessel mounting structure is available for sealably mounting a cylindrical window section so as to accommodate variations in pressure and temperature while permitting connection to all chamber utilities through a non-end portion mounting structure, while also providing internal mounting surfaces for securing internal chamber utilities therewith and while further providing a structure for supporting the pressure vessel separate and apart from the end portions thereof.

SUMMARY OF THE INVENTION

The present invention relates to a new and improved mounting structure for a cylindrical window section of a pressure vessel, the mounting structure having a cylindrical outer band, a mounting block within the outer band, structure for securing the outer band and mounting block with the pressure vessel, and a seal member positioned within the outer band and adjacent to the mounting block, with the seal member being axially movable with respect to the outer band for maintaining a sealable engagement of the cylindrical window section between the seal member and the end portion of the pressure vessel.

DESCRIPTION OF THE PREFERRED EMBODIMENTS

The mounting structure of the present invention is generally designated with the letter M. The mounting structure M is adapted to be used with a pressure vessel V. Pressure vessel V generally includes cylindrical window sections W and end portions E. The mounting structure M includes generally a cylindrical outer band O, a mounting block B mountable within the outer band O, securing means G for securing the outer band O and mounting block B with the pressure vessel V, and a seal member S mounted within the outer band O adjacent the mounting block B for engaging the cylindrical window section W to maintain a sealable relationship between the seal member S and the end portion E of the pressure vessel V.

Figure 1:
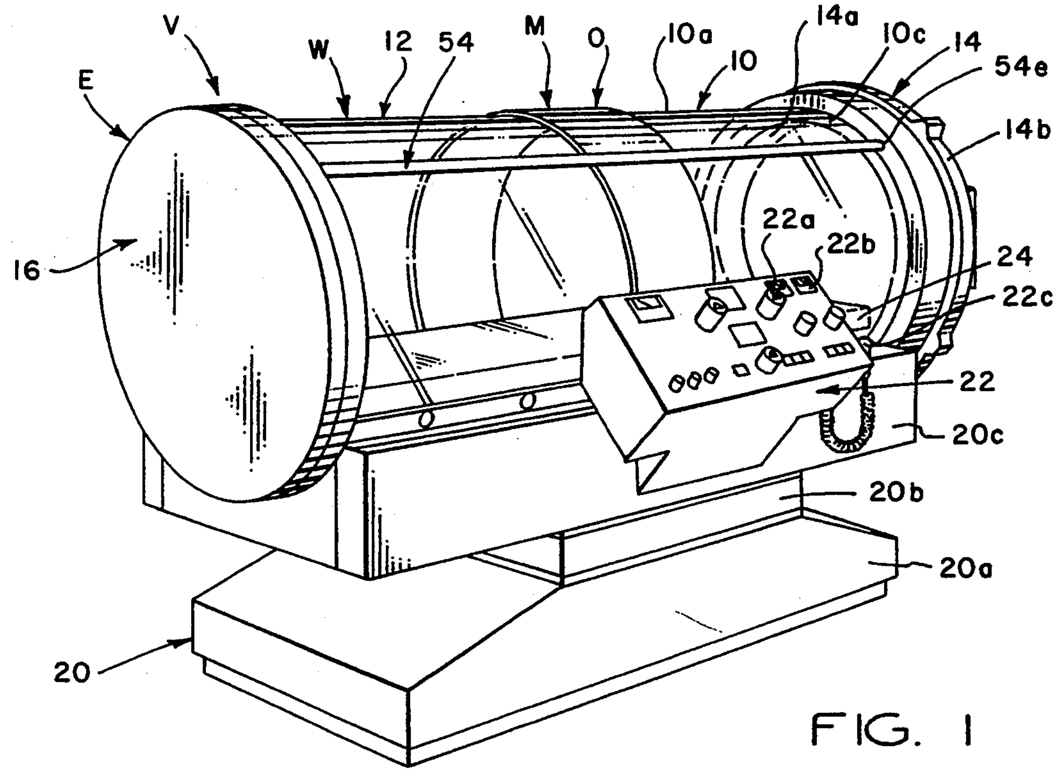
FIG. 1 is an isometric, perspective view of a pressure vessel, notably a hyperbaric chamber, of the type adapted to use the mounting structure of the present invention.
Figure 2:
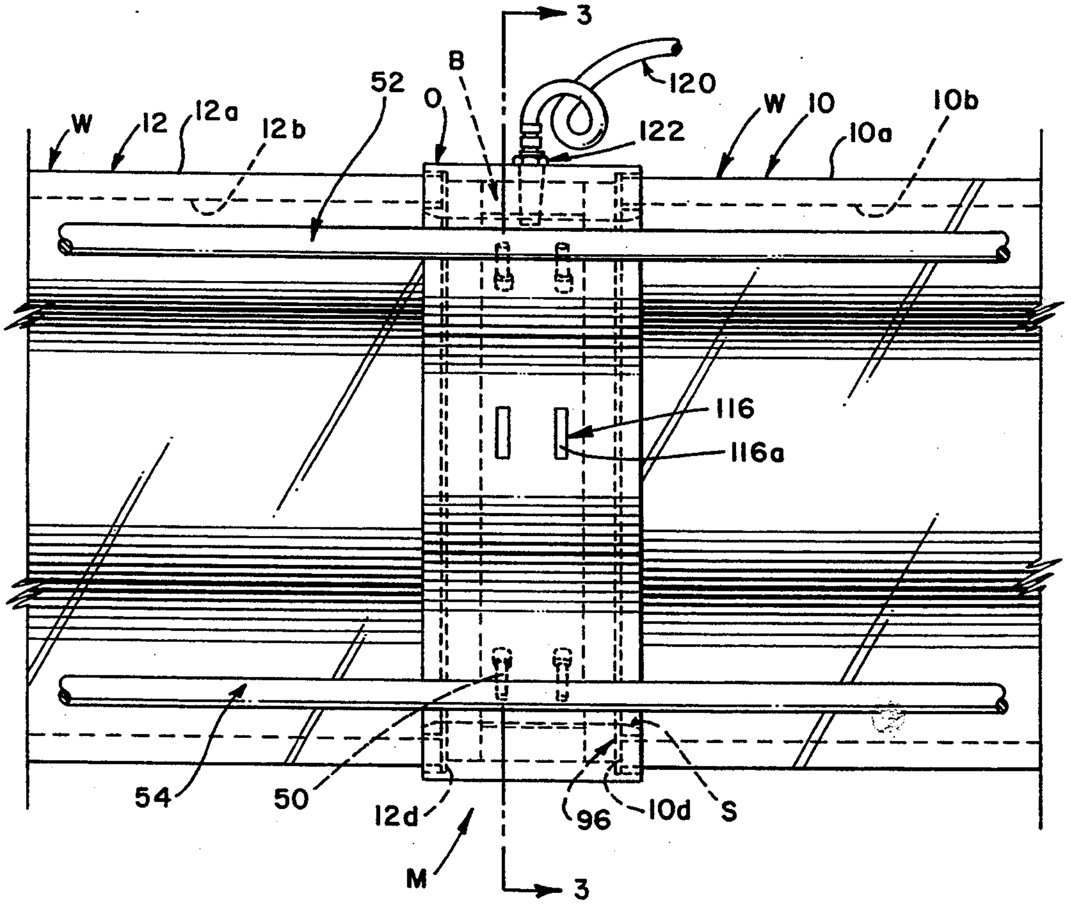
FIG. 2 is a top, sectional view of the pressure vessel, showing the mounting structure of the present invention.

The mounting structure M of the present invention is to be used with the pressure vessel V. As shown in FIG. 1, the pressure vessel V includes cylindrical window sections W which includes windows 10, 12 having an outer annular surfaces 10*a*, 12*a*, inner annular surfaces 10*b*, 12*b*, a first radial surface 10*c*, 12*c*, and a second radial surface 10*d*, 12*d*. Preferably, the windows 10, 12 of the cylindrical window section W are formed of a suitable, high strength polymeric material capable of withstanding the high internal pressures within pressure vessels V of the type that are typically used as hyperbaric chambers. For example, many hyperbaric chambers routinely operate at three atmospheres of internal pressure and for safety considerations are pressure tested to 4½ atmospheres. The pressure vessel V may be constructed having a single window 10, or utilizing dual windows 10, 12 as shown in the figures. Additional, multiple window sections (not shown) may be used if desired.

The pressure vessel V further includes end portions E which may include a closure member 14 and an end plate 16. The closure member 14 may be of the type described in my pending application Ser. No. 08/118002, filed Sept. 9, 1993, entitled "CLOSURE MEMBER FOR PRESSURE VESSEL" and includes generally a pressure vessel door 14*a* and a ring assembly 14*b*. The ring assembly 14*a* interacts with the pressure vessel door 14*a* to permit a locked or unlocked condition as may be desired. In typical operation, the pressure vessel door 14*a* may be opened to allow access into the chamber 18 (FIG. 3) within the pressure vessel V, with the pressure vessel door 14*a* thereafter being adapted to be closed. The ring assembly 14*b* is rotatable from an unlocked position to a locked position so that the closed pressure vessel door 14*a* is maintained in a lockable, sealable relationship therewith so as to permit pressurizing the pressure vessel V. The end plate 16 of the end portion E may be formed of stainless steel or any other suitable high strength material as may be desired.

As discussed more fully hereinbelow, the pressure vessel V, including the cylindrical window section W, end portions E and mounting structure M are adapted to be supported by base structure 20 which may include a floor platform 20*a*, a central support 20*b* and pressure vessel platform 20*c*. The floor platform 20*a* may be permanently secured to the floor or, in the alternative, may be mounted on rollers or other suitable means for moving the pressure vessel V as may be desired. The central support 20*b* is sized so as to elevate the pressure vessel V to a proper working height so that ease of access is provided to the attendant for manipulation of control knobs 22*a* of the control panel 22, for monitoring the various gauges 22*b*, for utilizing the communications equipment 22*c* and also enhancing ease of access to the patient bed 24. Preferably, the control panel 22 is mounted with the pressure vessel platform 20*c*, with the pressure vessel platform 20*c* also supporting the pressure vessel V. The patient bed 24 is preferably positioned on rollers (not shown) and supported on rails (not shown) mounted with the pressure vessel V. The patient bed 24 may be fully extended outwardly from within the chamber 18 of the pressure vessel V when the pressure vessel door 14*a* of the closure member 14 is in a fully open position so as to permit attendant access to the patient either on, to be placed upon or removed from the patient bed 24. The patient bed 24 may thereafter be re-positioned within chamber 18 of the pressure vessel V and the pressure vessel door 14*a* thereafter properly secured for hyperbaric treatment of the patient. The control panel 22 contains all the various attendant controls necessary for monitoring and safely operating the pressure vessel V.

Figures 5, 5A:
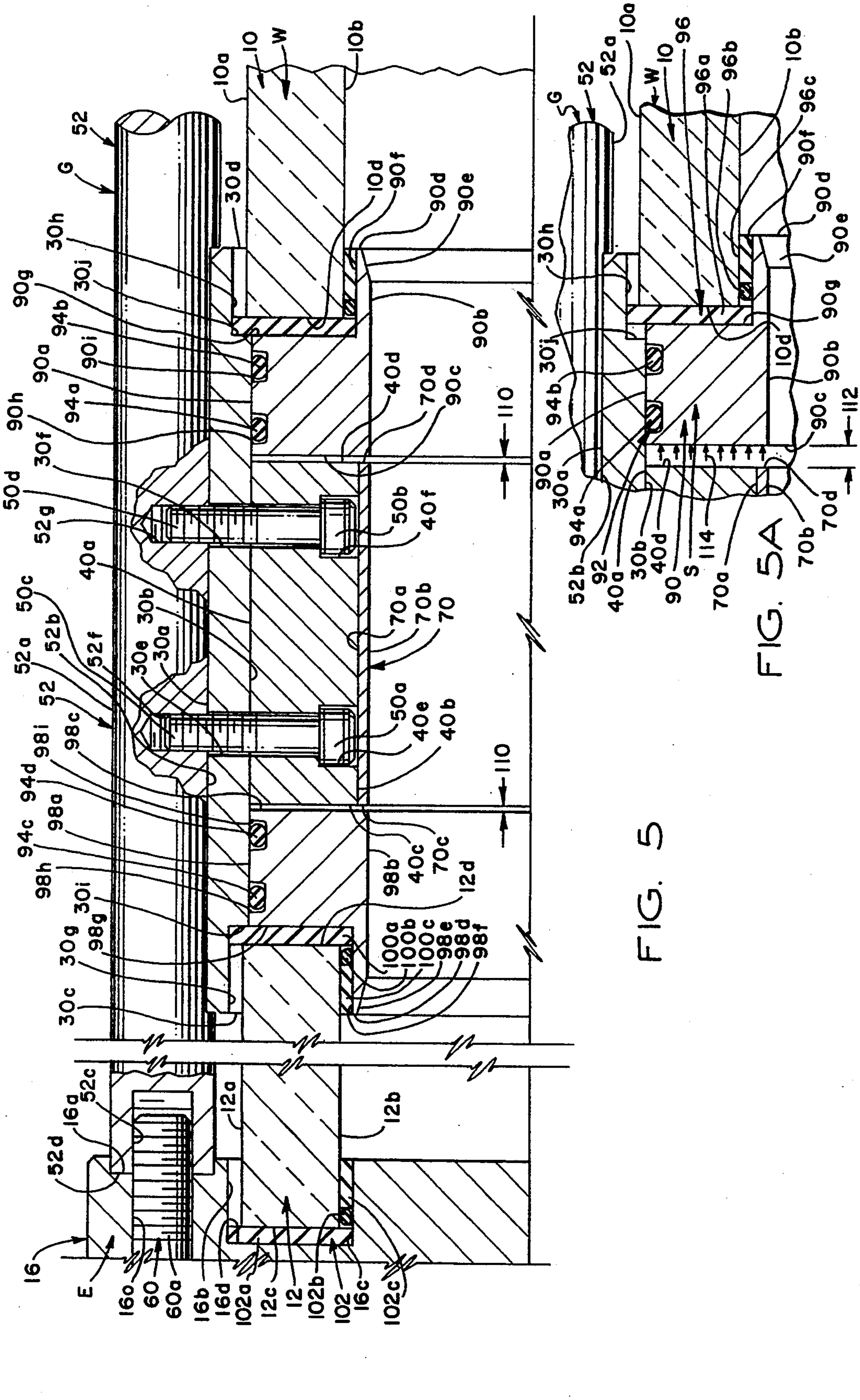
FIG. 5 is a sectional view of the mounting structure of the present invention, as taken along the lines 5—5 of FIG. 3.
FIG. 5A is a sectional detail of the seal member of the mounting structure of the present invention, as illustrated in an elevated, pressured condition as compared with that as shown in FIG. 5; and, FIG. 6 is a sectional view of the mounting structure of the present invention, similar to FIG. 5, showing an alternative embodiment of the seal member and outer band of the mounting structure of the present invention.

The mounting structure M of the present invention includes an outer band 30 which is preferably of a cylindrical configuration, having an outer annular band surface 30*a*, and an inner annular band surface 30*b*, and radial end surfaces 30*c*, 30*d* formed at the extremities of and joining the inner and outer annular band surfaces 30*a*, 30*b*. Preferably suitable openings 30*e*, 30*f* (FIG. 5, FIG. 6) are formed extending between the inner and outer annular band surfaces 30*a*, 30*b*. As best seen in FIG. 5, annular surfaces 30*g*, 30*h* and adjacent radial surfaces 30*i*, 30*j*, respectively, are formed adjacent radial end surfaces 30*c*, 30*d*, respectively.

Figure 3:
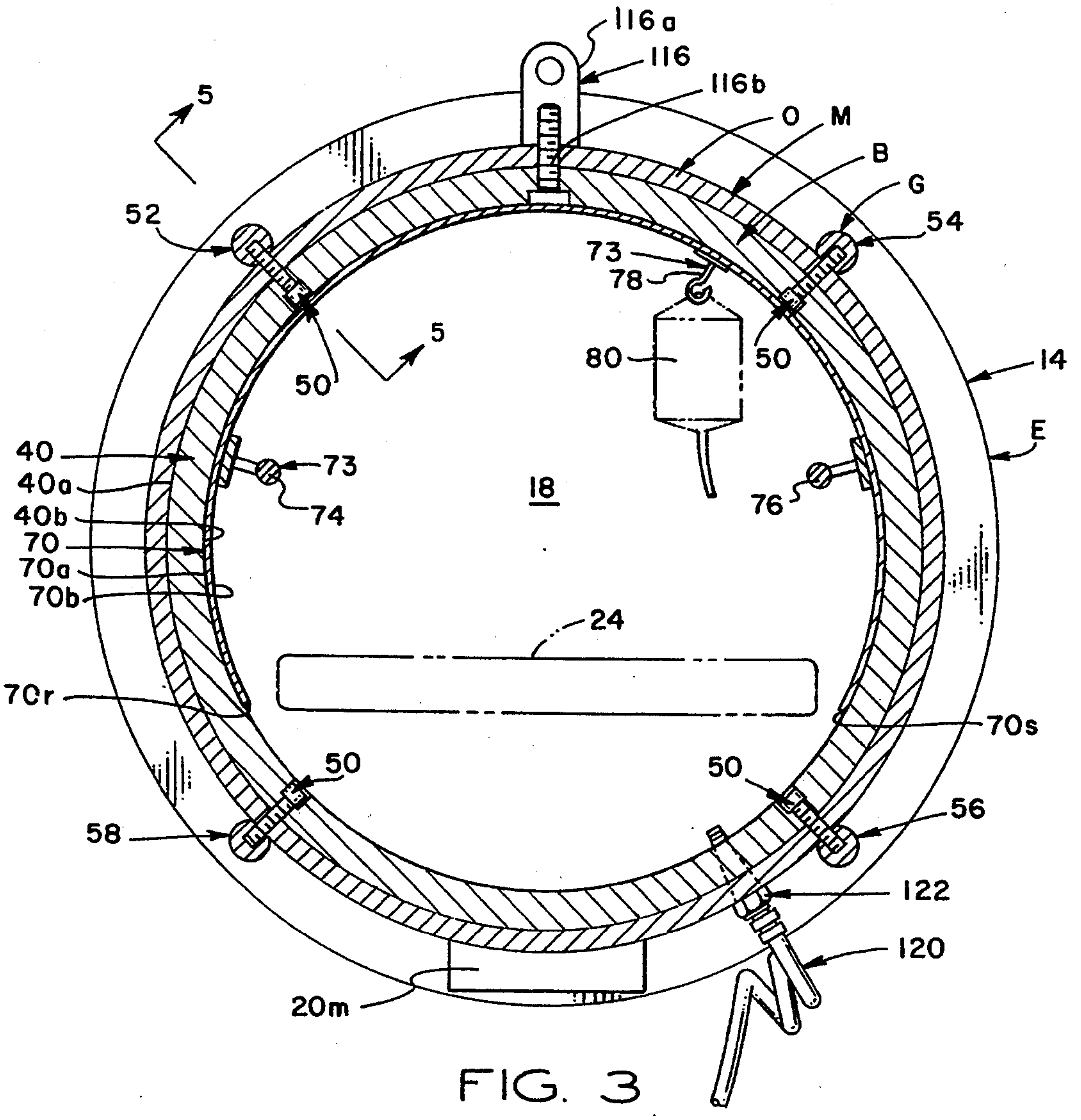
FIG. 3 is an elevational view of the mounting structure of the present invention, as taken along the lines 3—3 of FIG. 2.
Figure 4:
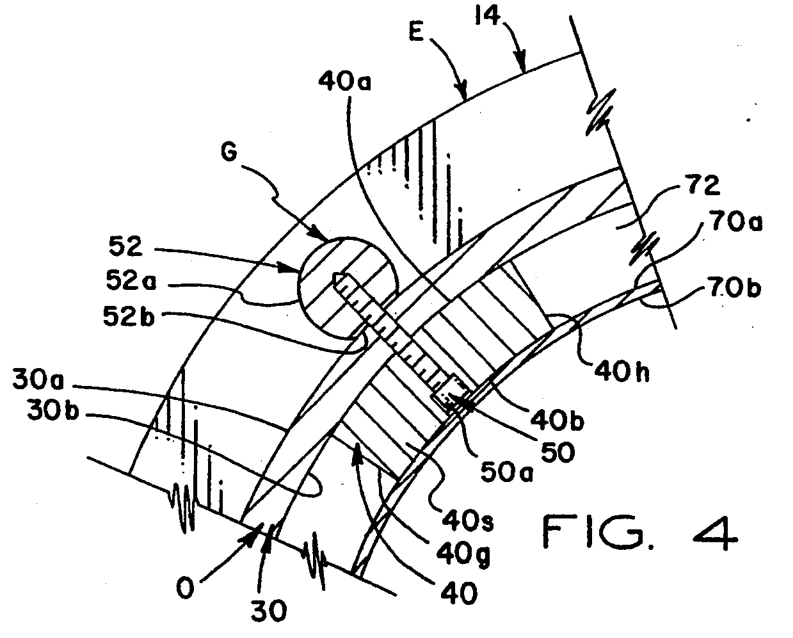
FIG. 4 is an elevational, enlarged, sectional view of the securing means of the mounting structure of the present invention.

The mounting structure M of the present invention may preferably further include a mounting block B which includes mounting block 40. The mounting block 40 includes an outer annular block surface 40*a*, an inner block surface 40*b* and radial end surfaces 40*c*, 40*d*. Stepped openings 40*e*, 40*f* are formed in the block 40 and adapted to be sized and aligned with openings 30*e*, 30*f*, respectively formed in outer band 30. The outer annular block surface 40*a* is adapted to be positioned adjacent to inner annular band surface 30*b* of the outer band 30. As shown in FIG. 3, the mounting block 40 may be of a substantially continuous cylindrical configuration as viewed in a plane substantially perpendicular to the axial length of the pressure vessel V. As shown in FIG. 4, the mounting block 40 may alternatively be of a segmented circular cross-sectional configuration, with such arcuate block sections 40*s* having radial surfaces 40*g*, 40*h*.

The mounting structure M of the present invention further includes securing means G for securing the outer band O and the mounting block B at predetermined fixed axial distance from the end portions E of the pressure vessel V. The securing means G is mounted with the pressure vessel V and includes securing fasteners 50 and tie rods 52, 54, 56, 58 (FIG. 3). Preferably, each of the tie rods 52, 54, 56, 58 are formed alike. For example, tie rod 52 is formed having an outer annular surface 52*a*, with an intermediate engaging surface 52*b* (FIG. 4) formed adjacent to the area of engagement of the outer annular band surface 30*a* of the outer band 30 of the outer band 0. Preferably, the tie rods 52, 54, 56, 58 are secured with the end portions E of the pressure vessel V by tie rod fasteners 60 such as fastener 60*a* (FIG. 5). The fastener 60*a* extends through opening 16*o* formed in end plate 16 of the end portion E to be received in compatibly formed threaded portion 52*c* formed adjacent end 52*d* of tie rod 52. The end 52*d* of tie rod 52 is received in a suitably formed tie rod detent, such as tie rod detent 16*a* formed in end plate 16. Like tie rod fasteners are used for fastening each of the ends of the tie rods 52, 54, 56, 58 with the end plate 16 and the other ends (such as tie rod end 54*e*) with the closure member 14 (FIG. 1), with each of such tie rod fasteners (not shown) being threadedly received in compatibly formed threaded portions (not shown). As such, each of the tie rods 52, 54, 56, 58 are secured with the end portions E of the pressure vessel V, including at one end with the closure member 14 and at the other, with end plate 16. Securing fasteners 50, such as fasteners 50*a*, 50*b* having respective threaded portions 50*c*, 50*d* are mountable within stepped openings 40*e*, 40*f* formed in mounting block 40, through aligned openings 30*e*, 30*f* in outer band 30 and thereafter threadedly received in threaded openings 52*f*, 52*g* formed adjacent engaging surface 52*b* in the tie rod 52 for affixing the mounting block 40 and outer band 30 securely with the tie rod 52 of the securing means G. As a result of the securing fasteners 50 and tie rod fasteners 60, the mounting block 40 of the mounting block B and the outer band 30 of the outer band O are fixed at a predetermined axial distance from the end portions E of the pressure vessel V.

The mounting structure M of the present invention may preferably further include a cover plate 70 having an outer plate surface 70*a*, inner plate surface 70*b* and end surfaces 70*c*, 70*d*. The cover plate 70 is adapted to be positioned so that the outer plate surface 70*a* engages the inner block surface 40*b* of the mounting block 40 and is sized so that the end surfaces 70*c*, 70*d* are in alignment with end surfaces 40*c*, 40*d* of the mounting block 40 of the mounting block B. In the event that the mounting block 40 is of a continuous cylindrical configuration as shown in FIG. 3, then the outer plate surface 70*a* of the cover plate 70 engages the inner block surface 40*b* of the mounting block adjacent the entire extent thereof. On the other hand, if the mounting block 40 is an arcuate block section 40*s* as shown in FIG. 4, then a cavity 72 is formed between the inner annular band surface 30*b*, the outer plate surface 70*a* of the cover plate 70 and end surfaces 40*g*, 40*h* of adjacent arcuate block sections 40*s*. Alternatively, an annular detent (not shown) may be formed in either the outer annular block surface 40*a* or the inner block surface 40*b* for forming a cylindrical cavity as may be desired. Such a cavity 72 may be useful for mounting various pressure vessel utilities (wiring, fluids, etc.) for utilization of the pressure vessel V of the present invention. Furthermore, the cover plate 70, or in the absence thereof the mounting block 40, provides suitable structure for mounting pressure vessel apparatus 73, such as handrails 74, 76 (FIG. 3) within the chamber 18, and a variety of hooks, such as hook 78, for supporting fluid bags 80 or any number of other monitoring/life support devices connected to or for the patient within such a pressure vessel V. As best seen in FIG. 3, it is preferred that the cover plate 70 be formed so as to be less than 360° in cross section in a plane perpendicular to the axial length of the pressure vessel V. Thus, an opening is formed between surface portions 70*r*, 70*s* for ease of providing appropriate connections for the various pressure vessel apparatus 73, such as fluid bags 80 and/or monitoring/life support devices.

The mounting structure M of the present invention further includes a seal member S which includes a seal member 90. The seal member 90 includes an outer annular seal surface 90*a*, an inner seal surface 90*b*, radial end surface 90*c* and window engaging surface 90*d*. A tapered surface 90*e* may be formed between the window engaging surface 90*d* and inner seal surface 90*b*. The window engaging surface 90*d* may be formed having an annular surface 90*f* and radial surface 90*g*. Seal detents 90*h*, 90*i* receive outer band seal means 92, including band seals 94, such as seals 94*a*, 94*b*, respectively, for sealably engaging the seal member 90 with the inner annular band surface 30*b* of outer band 30.

The mounting structure M of the present invention further includes window seal means designated generally 96 disposed between the window engaging surface 90*d* of the seal member 90 and the cylindrical window sections W for establishing a sealable relationship therebetween. The window seal means 96 may include compressible packing 96*a*, such as that formed of neoprene, an o-ring 96*b*, such as those formed of Buna-N, and a cylindrical seal 96*c*, preferably formed of neoprene. Preferably, the compressible packing 96*a* is disposed between radial surface 90*g*, annular surface 90*f* of the window engaging surface 90*d*, the annular surface 30*h* and adjacent radial surface 30*i* of the outer band 30 and the second radial surface 10*d* of the window 10 (FIG. 5). The o-ring 96*b* of the seal means 96 preferably is disposed between the inner annular surface 10*b* of the window 10 and the annular surface 90*f* of the window seal member 90, with the cylindrical seal 96*c* likewise positioned adjacent thereto (FIGS. 5, 5A). Seal member 98 is a mirror image of the seal member 90, with seal member parts, 98*a* through 98*i*, denominating like parts with seal member 90. Seals 94*c*, 94*d* of the band seals 94 of the outer band seal means 92 sealably engage the seal member 98 with the inner annular band surface 30*b* of the outer band 30. Preferably, seal member 90 engages window 10 which abuts the closure member 14 of the end portion E. Seal member 98 having window seal means 100, with like parts denominating like elements for seal means 100 as with window seal means 96, engages window 14, which abuts end plate 16 of the end portion E. Thus, window seal means 96, 100 establish a sealable relationship between the window engaging surfaces 90*g*, 98*g* of seal members 90, 98 of the seal member S of the present invention with the windows 10, 12 of the cylindrical window sections w.

As best seen in FIG. 5, the end plate 16 is formed having annular surfaces 16*b*, 16*c* and an adjoining radial surface 16*d* for receiving the window 12, with suitable end seal means 102 disposed therebetween. The end seal means 102 includes compressible packing 102*a*, o-ring 102*b*, and cylindrical seal 102*c*, much like window seal means 96, 100. As such, the compressible packing 102*a* is disposed between the first radial surface 12*c* of window 12 and radial surface 16*d* of end plate 16 of the end portion E, as located between annular surfaces 16*b*, 16*c* formed at end plate 16. The o-ring 102*b* is preferably disposed between the inner annular surface 12*b* of window 12 and the annular surface 16*c* of end plate 16, with cylindrical seal 102*c* being likewise disposed between inner annular surface 12*b* and annular surface 16*c* and adjacent to o-ring 102*b*. As such, the window 12 is located between the end plate 16 of end portion E and seal member 98, while window 10 is disposed between closure member 14 of the end portion E and seal member 90.

Figure 6:
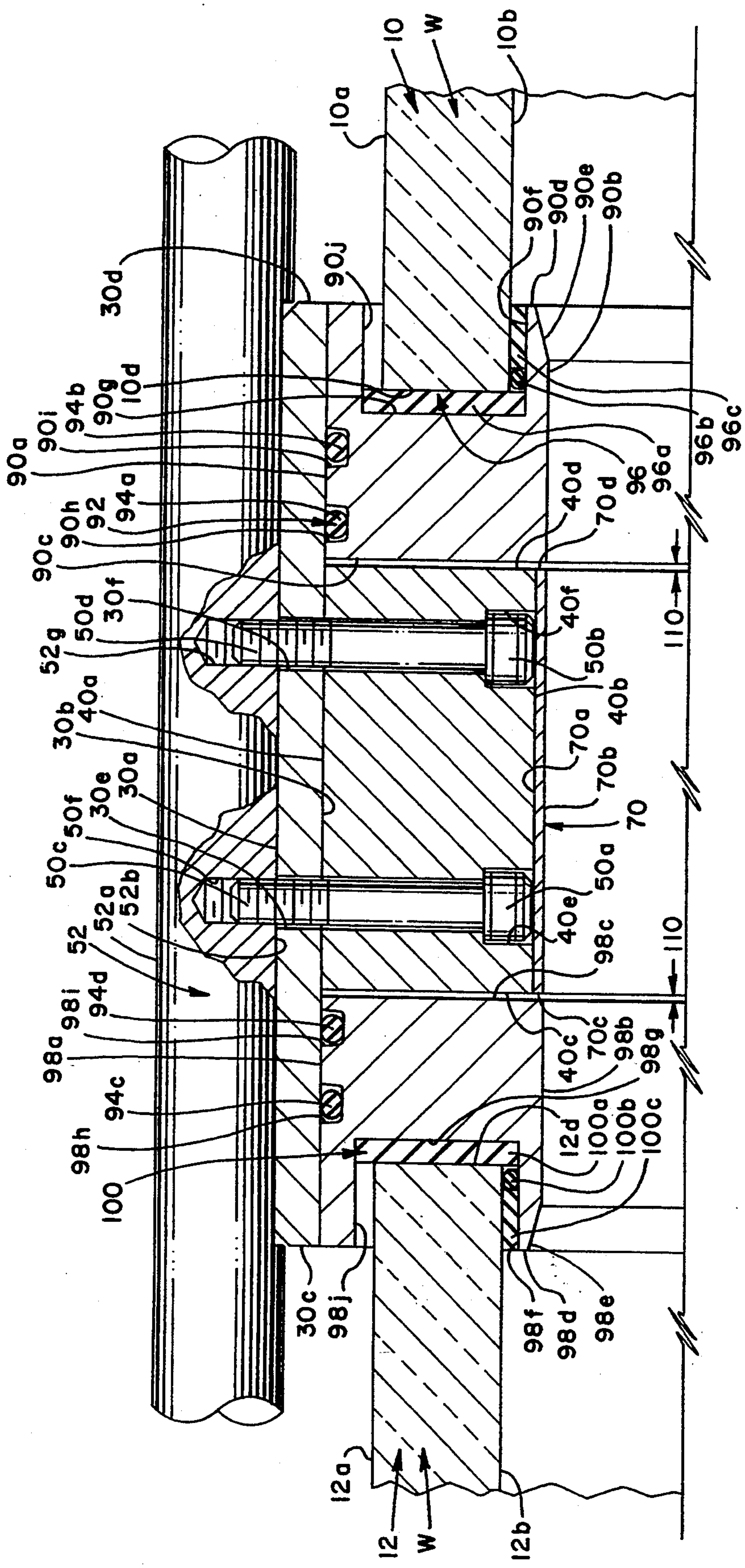

As best seen in FIG. 6, the outer band 30 and seal members 90, 98 may be of an alternate configuration. In this alternative configuration the outer band 30 has no annular surfaces 30*g*, 30*h* nor radial surfaces 30*i*, 30*j*, but rather has a continuous inner annular band surface 30*b* that spans between radial end surfaces 30*c*, 30*d*. With respect to the seal members 90, 98, the outer annular seal surfaces 90*a*, 98*a* extend between radial end surfaces 90*c*, 98*c* and window engaging surfaces 90*d*, 98*d*, with the seal members 90, 98 being sized so as to form annular surface 90*j*, 98*j* adjacent to radial surfaces 90*g*, 98*g* and annular surfaces 90*f*, 98*f*, for forming the respective window engaging surfaces 90*d*, 98*d*, respectively.

In the use or operation of the mounting structure M of the present invention, it is preferred that in the makeup of the pressure vessel V that the cylindrical window sections W be secured between the mounting structure M and the end portions E of the pressure vessel V. The seal members 90, 98 permit the windows 10, 12 to be snugly, but not necessarily in a sealably fluid-tight relationship, positioned between other pressure vessel V components that are securely affixed together, noting that the mounting block B, outer band O, tie rods and fasteners of the securing means G are all securely affixed with the end portions E of the pressure vessel V. When the pressure vessel V is pressurized, that is the closure member 14 is closed and locked and the pressure within the pressure vessel V is greater than that of the outside pressure, the internal pressure within the chamber 18 acts on radial end surfaces 90*c*, 98*c* of the seal members 90, 98, thus urging each of the seal members 90, 98 towards the respective closure member 14, end plate 16 of the end portions E. This action results in the windows 10, 12 being sealably engaged with the seal members 90, 98 via window seal means 96, 100 as the seal members 90, 98 are urged axially away from the mounting block B and towards their respective end portions E. Indeed, under pressure, the gap 110 (FIGS. 5, 6) increases to a greater gap 112 (FIG. 5A) as a result of the pressure acting on radial end surfaces 90*c*, 98*c*. In FIG. 5A, the pressure is depicted by the arrows 114 as such acts on radial end surface 90*c*. Under such a circumstance, the compressible packing 96*a* may move away from radial surface 30*j*, as shown in FIG. 5A, in accommodating the axial movement of the seal member 90. The ability for the seal members 90, 98 to move axially permits a sealable relationship to be maintained with the windows 10, 12, despite variations in pressure and temperature which can affect the overall dimension and/or sizing of such windows 10, 12 of the cylindrical window sections W. This axial movement also permits less critical axial sizing of the various component parts of the pressure vessel V in the makeup/assembly of the windows 10, 12, closure member 14, end plate 16, and tie rods 52, 54, 56, 58, respectively. Furthermore, as shown in FIG. 5, when the seal member 98 moves axially away from the mounting block B towards end plate 16 of the end portion E, the window 12 is further forced into a sealable relationship with the end seal means 102 including the compressible packing 102*a*, o-ring 102*b* and cylindrical seal 102*c*, recognizing that pressure within the chamber 18 also acts upon cylindrical seals 102*c*, 100*c* and o-rings 102*b*, 100*b* to force such seals into a sealable relationship with the inner annular surface 12*b* of window 12 and respective annular surfaces 98*f*, 16*c*.

It will be appreciated that utilization of the mounting structure M of the present invention may be used with a pressure vessel V having a single cylindrical window section W or a pressure vessel V having two windows 10, 12 as depicted in the drawings. Additional cylindrical window sections W may also be used by interposing an additional mounting structure M between adjacent window sections W of the pressure vessel V, as may be desired. Alternatively, the mounting structure M may be positioned adjacent one or both of the end portions E of the pressure vessel V, if so desired.

As a result of the mounting structure M of the present invention, pressure vessel apparatus 73 such as handrails 74, 76, hooks 78, and other useful devices typically needed within hyperbaric chambers, may be easily mounted and secured within the chamber 18 of the pressure vessel V. To the extent prior art pressure vessels use a continuous cylindrical window along the entire length of the pressure vessel V, because structural weakening and/or stress concentrations, no such items are mountable on the interior surface of a continuously formed cylindrical window.

Furthermore, the structural arrangement of the mounting block B, outer band 0 and tie rod/fasteners of the securing means G affixation with the end portions E of the pressure vessel V, permits the mounting structure M of the present invention to become a support point for the entire pressure vessel V. Prior art pressure vessels utilizing a singular continuous cylindrical window rely upon pressure vessel support adjacent the end portions, with any portion of the cylindrical window being prohibited from supporting the pressure vessel V because of structural strength considerations. By use of the mounting structure M of the present invention, the pressure vessel V may be supported entirely by the mounting structure M by use of a base structure mount 20*m* (FIG. 3) of the base structure 20 or, in the alternative, the entire pressure vessel V may be suspended by suitable vertical support (not shown) that connects with the mounting structure M of the present invention via vertical support members 116. The vertical support members 116 may each include a support 116*a* that is affixed to the outer annular band surface 30*a* of the outer band 30 by fastener 116*b*. By supporting the pressure vessel V with support members 116, the floor areas proximate the pressure vessel V are made available for other uses, thus avoiding the need and requirement of end portion E support. All hyperbaric chamber utilities are capable of being routed into the chamber 18 via the mounting structure M with all of the various components capable of being routed through cavities, such as the cavity 72 (FIG. 4). Furthermore, a pressurizing line 120 may be affixed with the mounting structure M by a suitable pressure connector 122 which communicates with the chamber 18 within the pressure vessel V. Such a connection would not be possible in a pressure vessel V formed solely of a cylindrical window W, as any opening penetrating the wall thickness of such a window compromises the strength and integrity of such a window.

Thus, the mounting structure M of the present invention provides a new and improved structure for securing a cylindrical window W with a pressure vessel V, permitting ease of assembly, increased internal mounting surfaces for chamber utilities and for centralizing the support and strength of the overall pressure vessel V.

The foregoing disclosure and description of the invention are illustrative and explanatory thereof, and various changes in the size, shape and materials, as well as the details of the illustrated construction may be made without departing from the spirit of this invention.

What is claimed is:

1. A mounting structure for a cylindrical window section of a pressure vessel, the cylindrical window section having a first radial end surface and a second radial end surface, the pressure vessel having an end portion for sealably engaging the first radial end surface of the cylindrical window section, comprising:

a cylindrical outer band having an outer annular band surface and an inner annular band surface;

a mounting block having an outer annular block surface and an inner block surface, said outer annular block surface engaging said inner annular band surface;

securing means for securing said outer band and said mounting block a predetermined fixed axial distance from the end portion of the pressure vessel, said securing means mounted with the pressure vessel and said outer band;

a seal member having an outer annular seal surface and an inner seal surface, said seal member having a radial end surface and a window engaging surface formed between said outer annular seal surface and said inner seal surface, said outer annular seal surface positioned adjacent said inner annular band surface of said outer band, said radial end surface positioned adjacent said mounting block, and said window engaging surface for receivably engaging the second radial end surface of the cylindrical window section;

window seal means disposed between said window engaging surface of said seal member and the second radial end surface of cylindrical window sections for establishing a sealable relationship therebetween;

said outer band, said mounting block, said seal member and the cylindrical window section are axially aligned; and, said seal member is movable axially with respect to said mounting block in order to maintain sealable engagement of the cylindrical window section between said seal member and the end portion of the pressure vessel.

2. The mounting structure of claim 1, wherein:

said securing means includes at least one threaded fastener disposed in aligned openings formed in said mounting block, said outer band and said tie rod for securing said mounting block, said outer band and said tie rod theretogether.

3. The mounting structure of claim 1, wherein:

said mounting block is of a cylindrical cross-sectional configuration as viewed in a plane perpendicular to the axial length of the pressure vessel.

4. The mounting structure of claim 1, further including:

pressure vessel apparatus mountable with said inner block surface of said mounting block.

5. The mounting structure of claim 1, wherein:

said window engaging surface of said seal member is formed by an annular surface proximate said inner seal surface and a radial surface formed adjacent to said annular surface.

6. The mounting structure of claim 1, wherein:

said window engaging surface of said seal member is formed of a first annular surface proximate said inner seal surface, a second annular surface proximate said outer annular seal surface and a radial surface formed adjacent to and between said first and second annular surfaces.

7. The mounting structure of claim 1, further including:

outer band seal means with said outer annular seal surface of said seal member for sealably engaging said inner annular band surface of said outer band.

8. The mounting structure of claim 1, further including:

supporting means with said securing means for supporting the pressure vessel.

9. The mounting structure of claim 1, further including:

supporting means with said outer band for supporting the pressure vessel.

10. The mounting structure of claim 1, wherein:

said outer annular band surface is of a greater diameter than the diameter of the outer annular surface of the cylindrical window section.

11. The mounting structure of claim 10, wherein:

said inner annular band surface of said outer band and said outer annular block surface of said mounting block are of a smaller diameter than the diameter of the outer annular surface of the cylindrical window section.

12. The mounting structure of claim 10, wherein:

said inner annular band surface of said outer band and said outer annular block surface of said mounting block are of a greater diameter than the diameter of the outer annular surface of the cylindrical window.

13. The mounting structure of claim 1, further including:

a cover plate having an outer plate surface and an inner plate surface, said outer plate surface positioned adjacent said inner block surface of said mounting block for mounting therewith.

14. The mounting structure of claim 13, further including:

pressure vessel apparatus mountable with said inner plate surface of said cover plate.

15. The mounting structure of claim 1, wherein:

said mounting block is of a segmented circular cross-sectional configuration as viewed in a plane perpendicular to the axial length of the pressure vessel.

16. The mounting structure of claim 15, further including:

a cover plate having an outer plate surface and an inner plate surface, said outer plate surface positioned adjacent said inner block surface of said mounting block for mounting therewith;

at least two of said segmented circular mounting blocks are mounted with said inner annular band surface of said outer band in a spaced apart relation so as to form a cavity between said mounting blocks, said inner annular band surface of said outer band and said outer plate surface of said cover plate.

17. The mounting structure of claim 1, wherein said securing means further includes:

at least one tie rod, said tie rod mountable with said outer annular band surface of said outer band and the end portion of the pressure vessel.

18. The mounting structure of claim 17, wherein said securing means further includes:

fastening means for securing said tie rod with said outer band and with the end portion of the pressure vessel.

19. The mounting structure of claim 17, wherein:

said tie rod is formed having an intermediate engaging surface for engagement with said outer annular band surface of said outer band.

20. A mounting structure for a pressure vessel having two cylindrical window sections, each of the cylindrical window sections having a first radial end surface and a second radial end surface, the pressure vessel having a first and a second end portion for sealably engaging the first radial end surfaces of each of the cylindrical window sections, comprising:

a cylindrical outer band having an outer annular band surface and an inner annular band surface;

a mounting block having an outer block surface and an inner block surface, said outer block surface engaging said inner annular band surface;

securing means for securing said outer band and said mounting block a predetermined fixed axial distance between the end portions of the pressure vessel, said securing means mounted with the pressure vessel and said outer band;

first and second seal members, each of said seal members having an outer annular seal surface, and an inner seal surface, each of said seal member having a radial end surface and a window engaging surface formed between said outer annular seal surface and said inner seal surface, said outer annular seal surfaces of said seal members positioned adjacent said inner annular band surface of said outer band, said radial end surfaces of said seal members positioned adjacent said mounting block, and said window engaging surfaces of said seal members receivably engaging the second radial end surfaces of the cylindrical window sections;

window seal means disposed between said window engaging surfaces of said seal members and the second radial end surfaces of the cylindrical window sections for establishing a sealable relationship therebetween;

said outer band, said mounting block, said first and second seal members, and the cylindrical window sections are axially aligned; and, said seal members are movable axially with respect to said mounting block in order to maintain sealable engagement of the cylindrical window sections between said seal members and the end portions of the pressure vessel.

21. The mounting structure of claim 20; wherein:

said securing means includes at least one threaded fastener disposed in aligned openings formed in said mounting block, said outer band and said tie rod for securing said mounting block, said outer band and said tie rod theretogether.

22. The mounting structure of claim 20, wherein:

said mounting block is of a cylindrical cross-sectional configuration as viewed in a plane perpendicular to the axial length of the pressure vessel.

23. The mounting structure of claim 20, wherein:

said mounting block is a segmented circular cross-sectional configuration as viewed in a plane perpendicular to the axial length of the pressure vessel.

24. The mounting structure of claim 20, further including:

pressure vessel apparatus mountable with said inner block surface of said mounting block.

25. The mounting structure of claim 20, wherein:

said window engaging surface of said seal member is formed by an annular surface proximate said inner seal surface and a radial surface formed adjacent to said annular surface.

26. The mounting structure of claim 20, wherein:

said window engaging surface of said seal member is formed of a first annular surface proximate said inner seal surface, a second annular surface proximate said outer annular seal surface and a radial surface formed adjacent to and between said first and second annular surfaces.

27. The mounting structure of claim 20, further including:

outer band seal means with said outer annular seal surface of said seal member for sealably engaging said inner annular band surface of said outer band.

28. The mounting structure of claim 20, further including:

supporting means with said outer band for supporting the pressure vessel.

29. The mounting structure of claim 20, further including:

supporting means with said securing means for supporting the pressure vessel.

30. The mounting structure of claim 20, further including:

a cover plate having an outer plate surface and an inner plate surface, said outer plate surface positioned adjacent said inner block surface of said mounting block for mounting therewith.

31. The mounting structure of claim 30, further including:

a cover plate having an outer plate surface and an inner plate surface, said outer plate surface positioned adjacent said inner block surface of said mounting block for mounting therewith;

at least two of said segmented circular mounting blocks are mounted with said inner annular band surface of said outer band in a spaced apart relation so as to form a cavity between said mounting blocks, said inner annular band surface and said outer plate surface of said cover plate.

32. The mounting structure of claim 31, further including:

pressure vessel apparatus mountable with said inner plate surface of said cover plate.

33. The mounting structure of claim 20, wherein:

said outer annular band surface is of a greater diameter than the diameter of the outer annular surface of the cylindrical window sections.

34. The mounting structure of claim 33, wherein:

said inner annular band surface of said outer band and said outer annular block surface of said mounting block are of a smaller diameter than the diameter of the outer annular surface of the cylindrical window sections.

35. The mounting structure of claim 33, wherein:

said inner annular band surface of said outer band and said outer annular block surface of said mounting block are of a greater diameter than the diameter of the outer annular surface of the cylindrical window sections.

36. The mounting structure of claim 20, wherein said securing means further includes:

at least one tie rod, said tie rod mountable with said outer annular band surface of said outer band and the end portions of the pressure vessel.

37. The mounting structure of claim 36, wherein said securing means further includes:

fastening means for securing said tie rod with said outer band and with the end portions of the pressure vessel.

38. The mounting structure of claim 36, wherein:

said tie rod is formed having an intermediate engaging surface for engagement with said outer annular band surface of said outer band.

* * * * *